US011460394B2

United States Patent
Minamitani (10) Patent No.: US 11,460,394 B2
(45) Date of Patent: Oct. 4, 2022

(54) CORROSIVE ENVIRONMENT MONITORING METHOD AND CORROSIVE ENVIRONMENT MONITORING SYSTEM

(71) Applicant: Hitachi, Ltd., Tokyo (JP)

(72) Inventor: Rintarou Minamitani, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 17/267,605

(22) PCT Filed: Jan. 29, 2019

(86) PCT No.: PCT/JP2019/002891
§ 371 (c)(1),
(2) Date: Feb. 10, 2021

(87) PCT Pub. No.: WO2020/039611
PCT Pub. Date: Feb. 27, 2020

(65) Prior Publication Data
US 2021/0325296 A1 Oct. 21, 2021

(30) Foreign Application Priority Data
Aug. 23, 2018 (JP) .............................. JP2018-156340

(51) Int. Cl.
*G01N 17/04* (2006.01)
*G06T 7/90* (2017.01)
(Continued)

(52) U.S. Cl.
CPC ......... *G01N 17/04* (2013.01); *G01N 33/0044* (2013.01); *G06K 9/6267* (2013.01);
(Continued)

(58) Field of Classification Search
CPC .. G01N 17/04; G01N 33/0044; G01N 17/043; G01N 31/224; G06K 9/6267;
(Continued)

(56) References Cited

U.S. PATENT DOCUMENTS

| 2011/0064967 A1* | 3/2011 | Stachowiak ............ C23C 28/00 428/457 |
| 2014/0190239 A1* | 7/2014 | Minamitani ....... G01N 33/0004 73/31.01 |

(Continued)

FOREIGN PATENT DOCUMENTS

| JP | S63-305232 A | 12/1988 |
| JP | H07-151738 A | 6/1995 |

(Continued)

OTHER PUBLICATIONS

Minamitani et al., "Elucidation of Silver Atmospheric Corrosion Mechanismsand Proposal for Corrosion Prediction Method", Proceedings of JSCE materials and Environments 2014, Japan Society of Corrosion Engineering, Apr. 2014, pp. 345-348, with partial translation.

(Continued)

*Primary Examiner* — Xuemei G Chen
(74) *Attorney, Agent, or Firm* — Foley & Lardner LLP (57) ABSTRACT

The present invention provides a corrosive environment monitoring method capable of short-term to long-term identification of the type of corrosive gas, without requiring a power source such as a commercial power source or a storage battery, in a narrow place inside an equipment housing of an electric or electronic device to be evaluated. The corrosive environment monitoring method of the present invention involves using a corrosion sensor that has a passage structure in which one end is closed and the other end is an opening, wherein a part of the upper and lower surfaces or left and right surfaces with respect to the opening is formed by a transparent substrate, and a metal thin film is formed on the surface of the transparent substrate that is in contact with the corrosive gas flowing in from the opening, observing the degree of discoloration of the metal thin film through the transparent substrate, and identifying the type of (Continued)

the corrosive gas from the relationship between the degree of discoloration and the type of corrosive gas that has been observed in advance.

7 Claims, 8 Drawing Sheets

(51) Int. Cl.
    *G01N 33/00*     (2006.01)
    *G06K 9/62*     (2022.01)
    *G06T 7/00*     (2017.01)
    *G06V 10/56*     (2022.01)

(52) U.S. Cl.
    CPC .............. *G06T 7/0002* (2013.01); *G06T 7/90* (2017.01); *G06V 10/56* (2022.01)

(58) Field of Classification Search
    CPC ..................... G06T 7/0002; G06T 7/90; G06T 2207/30136; G06T 7/0004; G06V 10/56
    See application file for complete search history.

(56) References Cited

U.S. PATENT DOCUMENTS

| | | | |
|---|---|---|---|
| 2015/0047879 A1* | 2/2015 | Shibuya | H01B 1/02 428/642 |
| 2015/0330889 A1* | 11/2015 | Minamitani | G01N 27/20 324/700 |
| 2016/0018338 A1* | 1/2016 | Song | G01N 31/221 156/60 |
| 2016/0114302 A1* | 4/2016 | Li | C01B 17/0248 252/363.5 |
| 2017/0160005 A1* | 6/2017 | Park | F25D 25/005 |
| 2018/0259442 A1* | 9/2018 | Minamitani | G01N 27/041 |
| 2019/0234994 A1* | 8/2019 | Endo | C22C 5/02 |
| 2020/0040131 A1* | 2/2020 | Fukamoto | C09J 163/00 |
| 2021/0301066 A1* | 9/2021 | Fujiwara | H05K 3/282 |

FOREIGN PATENT DOCUMENTS

| | | |
|---|---|---|
| JP | H09-126990 A | 5/1997 |
| JP | 2006-064466 A | 3/2006 |
| JP | 2006-145390 A | 6/2006 |
| JP | 2013-190241 A | 9/2013 |
| WO | WO-2017/175507 A1 | 10/2017 |

OTHER PUBLICATIONS

International Search Report with English translation and Written Opinion issued in corresponding application No. PCT/JP2019/002891 dated May 7, 2019.

* cited by examiner

CORROSIVE ENVIRONMENT MONITORING METHOD AND CORROSIVE ENVIRONMENT MONITORING SYSTEM

TECHNICAL FIELD

The present invention relates to a corrosive environment monitoring method and a corrosive environment monitoring system.

BACKGROUND ART

Electric or electronic devices require long-term reliability for stable operation. In addition, the electrical and electronic devices each employ a high-density package structure for speeding up and space saving and include many electrical and electronic components, each including a fine interconnection structure and/or a thin-film plating structure. Such an electrical and electronic component is changed in its electrical or magnetic properties due to slight corrosive damage, causing failure of malfunction of the component. Suppressing such corrosive damage is therefore a challenge to maintain and improve reliability of the electric or electronic device.

A cause of corrosion of the electric or electronic component includes corrosive gas. Sources of the corrosive gas include $SO_2$ caused by combustion of fossil fuel, $NO_2$ caused by exhaust gas from automobiles, $H_2S$ generated from domestic wastewater or waste, and $S_8$ generated from rubber and corrugated cardboard as components of the electric or electronic device.

An environment containing such a corrosive gas may concernedly induce corrosive damage of the electrical or electronic component and in turn reduce reliability of the electric or electronic device incorporating the electrical or electronic component. Recently, it is reported that corrosion trouble of a silver electrode of a chip part or a copper interconnection of a printed circuit board occurs due to reducing sulfur of $H_2S$ or $S_8$ (American Society of Heating, Refrigerating and Air-Conditioning Engineers (ASHRAE) TC9. 9, 2011 Gaseous and P1 articulate Contamination Guidelines For Data Centers).

The electric or electronic device must be installed in such a highly corrosive environment while a corrosion prevention measure is reflected on design or maintenance in correspondence to a degree of corrosiveness of environment. It is therefore required to specify a type of a corrosive gas in the environment in which the electric or electronic device is installed and simply and accurately evaluate corrosiveness of the environment in a short period.

Since the electric or electronic device requires space saving, a device to evaluate corrosiveness of environment is also required to be small and lightweight.

In this regard, as a method for evaluating corrosiveness of environment in which the electric or electronic device is installed, ISO 11844-1 employs a method of evaluating a corrosion degree of copper, silver, aluminum, iron, and zinc subjected to exposure for a certain period. Copper, silver, aluminum, iron, and zinc are each known to be corroded by any corrosive gas of $SO_2$, $NO_2$, and $H_2S$ while differing in degree of influence. In ISO 11844-1, a corrosion degree of metal subjected to exposure for one year is quantified by a gravimetric method, and a corrosion product of the exposed metal is quantified by an electrochemical measurement method.

Further, a background art of this technical field includes a technique of Japanese Patent No. 5798955 (patent literature 1). Japanese Patent No. 5798955 describes a corrosive environment monitoring device configured of a passage structure having one opening, in which a wall surface of part of the passage structure parallel to a diffusion direction of a corrosive substance from the opening is formed of a transparent substrate, and a metal thin film formed on the transparent substrate. The corrosive environment monitoring device is characterized in that a shape and a dimension of a region having a color, which is changed by a corrosion product of the metal thin film left in an environment to be measured for a predetermined period, can be measured through the transparent substrate, and the metal thin film is configured of a predetermined material.

CITATION LIST

Patent Literature

Patent literature 1: Japanese Patent No. 5798955.

SUMMARY OF INVENTION

Technical Problem

Patent literature 1 describes the corrosive environment monitoring device that evaluates corrosiveness of an environment in which an electric or electronic device is installed. The corrosive environment monitoring device described in patent literature 1 is configured of the passage structure having one opening, in which the wall surface of part of the passage structure parallel to the diffusion direction of the corrosive substance from the opening is formed of the transparent substrate, and the metal thin film formed on the transparent substrate, where length of a discolored region of the metal thin film is converted into a corrosion thickness in case of exposing a metal plate. $H_2S$ is assumed to exist from length of the discolored region of the metal thin film to evaluate corrosiveness of environment. An environment in which $H_2S$ is generated is therefore disadvantageously difficult to be discriminated from an environment in which $S_8$ is generated.

The present invention therefore provides a corrosive environment monitoring method and a corrosive environment monitoring system that are each capable of identifying a type of corrosive gas over both short and long periods without a power source such as a commercial power source and a storage battery in a narrow space inside a housing of an electric or electronic device to be evaluated. Specifically, the invention provides a corrosive environment monitoring method capable of identifying a type of corrosive gas without need of any special analytical equipment even in an environment in which an electric or electronic device is installed.

Solution to Problem

To solve the above-described problem, the corrosive environment monitoring method of the invention uses a corrosion sensor including a passage structure having a first end being closed and a second end as an opening, in which one of the upper and lower surfaces or left and right surfaces with respect to the opening is formed of a transparent substrate, and including a metal thin film formed on a surface of the transparent substrate, the surface being in contact with corrosive gas flowing in from the opening. In the method, the degree of discoloration of the metal thin film is observed through the transparent substrate, and a type of the corrosive gas is identified from a relationship between a beforehand observed degree of discoloration of the metal thin film and a type of the corrosive gas.

The corrosive environment monitoring system of the invention uses the corrosive environment monitoring method of the invention.

Advantageous Effects of Invention

According to the invention, there can be provided a corrosive environment monitoring method and a corrosive environment monitoring system that are each capable of identifying a type of corrosive gas over both short and long periods without a power source such as a commercial power source and a storage battery in a narrow space inside a housing of an electric or electronic device to be evaluated. Specifically, according to the invention, there can be provided a corrosive environment monitoring method capable of identifying a type of corrosive gas without need of any special analytical equipment even in an environment where an electric or electronic device is installed.

Other issues, configurations, and effects are clarified from the following description of embodiments.

DESCRIPTION OF EMBODIMENTS

One embodiment of the invention will now be described with reference to the drawings. Like reference numerals designate the same configurations, and duplicated description may be omitted.

First Embodiment

The first embodiment is directed to inside-and-outside environment, mainly an environment in which an electric or electronic device is installed, and identifies a type of corrosive gas contained in the environment, and measures the degree of corrosion of metal due to the corrosive gas.

Figure 1:
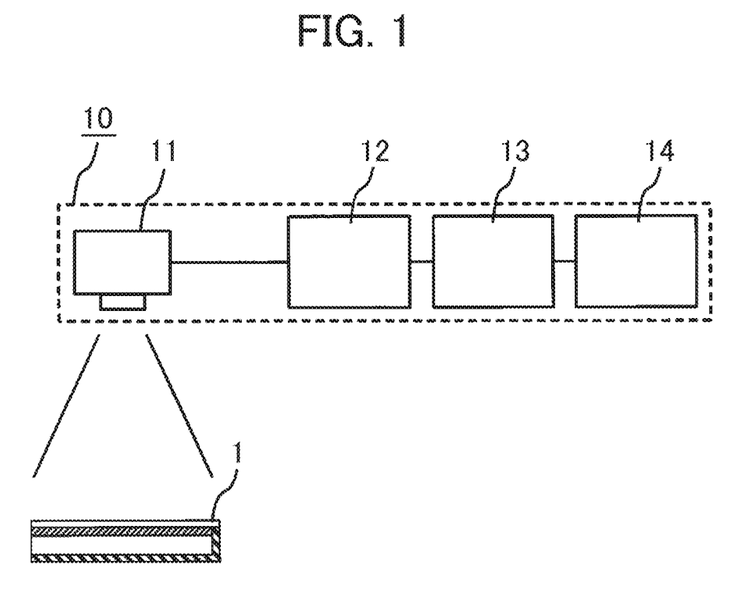
FIG. 1 is a schematic illustration of a corrosive environment monitoring system of this embodiment.

FIG. 1 is a schematic illustration of a corrosive environment monitoring system of the first embodiment.

The corrosive environment monitoring system described in the first embodiment incudes a corrosion sensor 1 and a determination system 10.

The determination system 10 includes a photographing unit 11 to take a photograph of a discoloration degree of a metal thin film (see FIG. 2) of the corrosion sensor 1, an image processing unit 12 that uses an image such as the photograph taken by the photographing unit 11 to digitize a discoloration degree of the metal thin film of the corrosion sensor 1, a calculation unit 13 that identifies a type of a corrosive gas from the discoloration degree of the metal thin film digitized by the image processing unit 12 and/or calculates the degree of corrosion of metal due to the corrosive gas, and an output unit 14 that outputs a result of calculation by the calculation unit 13.

The determination system 10 may be any system having respective functions of the photographing unit 11, the image processing unit 12, the calculation unit 13, and the output unit 14, and, for example, may be a mobile terminal such as smartphone.

Figure 2:
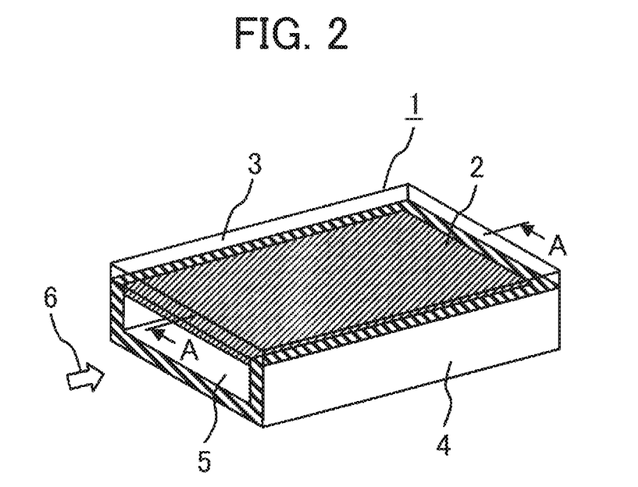
FIG. 2 is a perspective view of a corrosion sensor of the embodiment.

FIG. 2 is a perspective view of a corrosion sensor of the first embodiment.

The corrosion sensor 1 having a box shape includes a passage structure 4 having a first end being closed and a second end as an opening 5, in which one (the upper surface in the first embodiment) of the upper and lower surfaces or left and right surfaces with respect to the opening 5 is formed of a transparent substrate 3, and includes a metal thin film 2 formed on a surface in contact with the transparent substrate 3 and with the corrosive gas 6 flowing in from the opening 5. The degree of discoloration of the metal thin film 2 is observed through the transparent substrate 3.

Specifically, the rectangular corrosion sensor 1 includes the passage structure 4 having one surface as the opening 5 and a closed surface opposed to the opening 5 and thus having a hollow inside. The rectangular corrosion sensor 1 has the transparent substrate 3 on one surface (the upper surface in the first embodiment) of the upper and lower surfaces or left and right surfaces (other four surfaces) with respect to the opening 5. That is, the transparent substrate 3 is formed as one wall surface (the upper surface in the first embodiment) of the passage structure 4 parallel to a diffusion direction of the corrosive gas 6 flowing in from the opening 5. Further, the metal thin film 2 is formed on the surface in contact with the transparent substrate 3 and with the corrosive gas 6 flowing in from the opening 5.

A distance between the upper and lower surfaces with respect to the opening 5 (sometimes referred to as "distance between the transparent substrate 3 and the surface opposed to the transparent substrate 3" or "height of the opening 5") is preferably 0.5 to 2.0 mm. The distance (height) affects the amount of the corrosive gas 6 flowing into the opening 5, and specifically affects a discoloration degree of the metal thin film 2. Length from the opening 5 to the surface opposed to the opening 5 is determined in association with time (installation time) for installing the corrosion sensor 1 in the environment to be evaluated in corrosiveness. The length increases with an increase in the installation time. In the first embodiment, the distance (height) is set to 1.0 mm.

In the corrosion sensor 1, the metal thin film 2, configuring a sensor part, is formed on one inner wall surface (the upper surface in the first embodiment) of the passage structure 4. Specifically, the surface on which the metal thin film 2 is formed is formed such that the transparent substrate 3 is in contact with the corrosive gas 6 (located on a side of the atmosphere of the corrosive gas 6) in the passage structure 4, i.e., such that the metal thin film 2 can be observed through the transparent substrate 3. The metal thin film 2 preferably includes a metal having a color different from a color of a corrosion product of the metal, such as copper, silver, aluminum, iron, and zinc. In the first embodiment, silver is used for the metal thin film 2.

When the corrosion sensor 1 is exposed in an environment, the corrosive gas 6 in the environment flows in from the opening 5 and corrodes the metal thin film 2. At this time, the passage structure 4 affects a rate of corrosion of the metal thin film 2 as the sensor part due to the corrosive gas 6 in the environment. Specifically, height of the passage structure 4 (height of the opening 5) affects the amount of the corrosive gas 6 flowing into the passage structure 4, and as a larger amount of the corrosive gas 6 flows in, the corrosion rate of the metal thin film 2 increases. The height of the passage structure 4 (height of the opening 5) also affects a flow rate of the corrosive gas 6 flowing into the passage structure 4.

The passage structure 4 has only one opening 5, i.e., has no opening other than the opening 5, and is shielded from ambient environment except for the opening 5. A progress direction of corrosion of the metal thin film 2 is limited to one direction.

As described above, the corrosive environment monitoring method described in the first embodiment is primarily characterized by using the corrosion sensor 1 described in the first embodiment. The corrosion sensor 1, which is characterized by a type of the metal thin film 2 (silver is used in the first embodiment), thickness of the metal thin film 2 (preferably, 5 to 40 nm) and height of the opening 5 (preferably, 0.5 to 2.0 mm), identifies types of two corrosive gases $H_2S$ and $S_8$.

The corrosive environment monitoring method described in the first embodiment observes the degree of discoloration of the metal thin film 2 through the transparent substrate 3, and identifies a type of the corrosive gas 6 from a relationship between a beforehand observed degree of discoloration of the metal thin film 2 and the type of the corrosive gas 6.

The corrosive environment monitoring system described in the first embodiment includes the photographing unit 11 to photograph the discoloration degree of the metal thin film 2 of the corrosion sensor 1 described in the first embodiment, the image processing unit 12 that uses the image photographed by the photographing unit 11 to digitize the discoloration degree of the metal thin film 2, the calculation unit 13 that identifies a type of the corrosive gas from the discoloration degree of the metal thin film 2 digitized by the image processing unit 12 and the relationship between the beforehand observed degree of discoloration of the metal thin film 2 and the type of the corrosive gas 6, and the output unit 14 that outputs a result of calculation by the calculation unit 13.

Figure 3A:
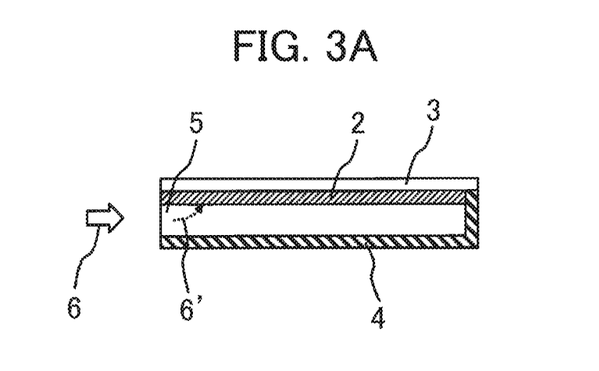
FIG. 3A is a sectional diagram along A-A, illustrating the corrosion sensor of the embodiment.
Figure 3B:
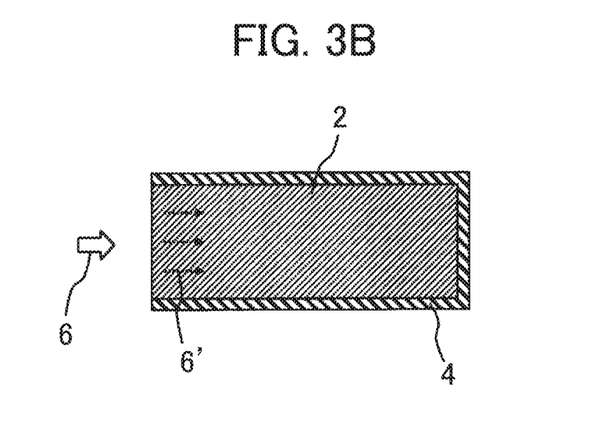
FIG. 3B is a top view of the corrosion sensor of the embodiment.

FIG. 3A is a sectional diagram along A-A, illustrating the corrosion sensor of the first embodiment. FIG. 3B is a top view of the corrosion sensor of the first embodiment.

Since the passage structure 4 is not a ventilation passage, the corrosive gas 6 in the environment gradually flows in from the opening 5 of the passage structure 4 with the lapse of time. Corrosive gas 6' represents the corrosive gas 6 flowing into the passage structure 4, and the corrosive gas 6' flowing into the passage structure 4 gradually comes into contact with the metal thin film 2 from an opening 5 side.

Figure 4A:
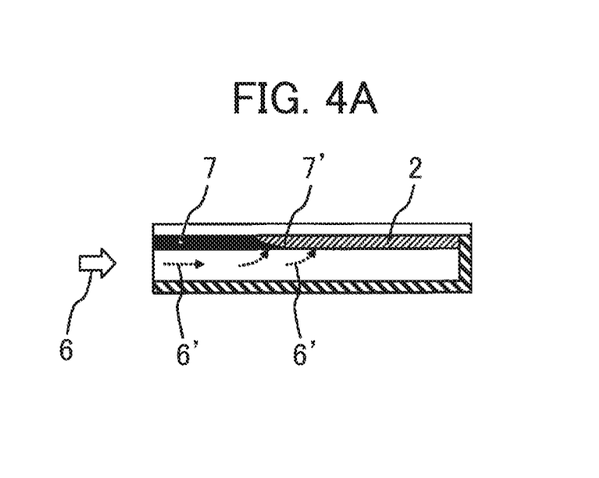
FIG. 4A is a sectional diagram along A-A, illustrating the corrosion sensor of the embodiment after exposure.
Figure 4B:
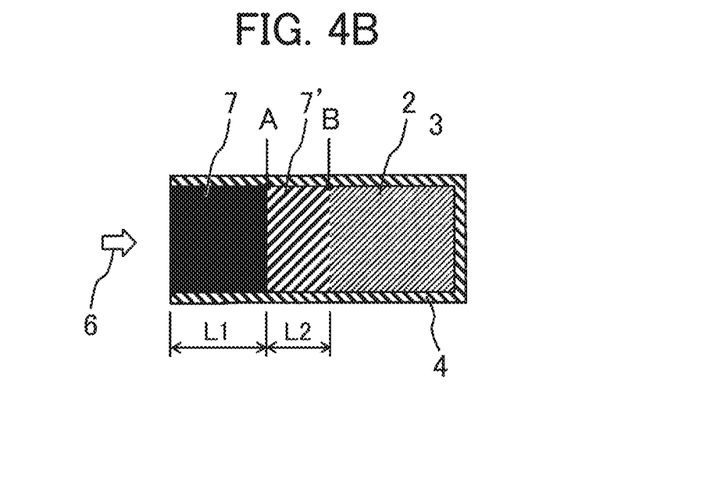
FIG. 4B is a top view of the corrosion sensor of the embodiment after exposure.

FIG. 4A is a sectional diagram along A-A, illustrating the corrosion sensor of the first embodiment after exposure. FIG. 4B is a top view of the corrosion sensor of the first embodiment after exposure.

FIGS. 4A and 4B each illustrate a corrosion state of the metal thin film 2 of the corrosion sensor 1 after exposure.

The corrosive gas 6 in the environment gradually flows in from the opening 5 of the passage structure 4 with the lapse of exposure time. The corrosive gas 6' represents the corrosive gas 6 flowing into the passage structure 4, and the corrosive gas 6' flowing into the passage structure 4 gradually comes into contact with the metal thin film 2 from the opening 5 side. The metal thin film 2 is gradually corroded from the opening 5 side with the lapse of exposure time.

With progress of corrosion of the metal thin film 2, corrosion thickness of the metal thin film 2 increases to the same thickness as the thickness of the metal thin film 2 in a region 7, which may be referred to as "region where the metal thin film 2 is corroded up to an interface with the transparent substrate 3" or "region where the metal thin film 2 is entirely corroded in a thickness direction. In the region 7, corrosion does not further progress in the thickness direction of the metal thin film 2.

The corrosive gas 6 in the environment diffuses from the left side close to the opening 5 (the left in FIG. 4) and gradually corrodes the metal thin film 2 toward the right side (the right in FIG. 4). The region 7 in which the metal thin film 2 is entirely corroded in the thickness direction (in FIG. 4, a range from the left end to the point A: length L1) gradually expands rightward with the lapse of exposure time. A region 7' in which the metal thin film 2 is partially corroded in the thickness direction (in FIG. 4, a range from the point A to the point B: length L2) gradually moves rightward with the lapse of exposure time.

Specifically, while the region 7, in which the metal thin film 2 is entirely corroded in the thickness direction, gradually expands rightward with the lapse of exposure time (the length L1 increases), the region 7', in which the metal thin film 2 is partially corroded in the thickness direction, gradually moves rightward with the lapse of exposure time (but the length L2 is not changed, i.e., the point B moves rightward in correspondence to rightward movement of the point A.

Description is now given on behavior of the corrosive gas 6' flowing into the passage structure 4 and diffusing in the vicinity of the opening 5. For the corrosion sensor 1, since the corrosive gas 6' is limitedly diffused in a direction from the left to the right, a progress direction of the metal thin film 2 is defined.

Since concentration of the corrosive gas 6' increases with a decrease in distance from the opening 5, a corrosion degree of the metal of the metal thin film 2 also increases at a shorter distance from the opening 5. Such behavior is described in "Visual Inspection Corrosion Sensor for Electronic Equipment", Zairyo-to-Kankyo, 67, 261-267(2018), which is introduced as reference.

In the first embodiment, the metal thin film 2 is used as the sensor part of the corrosion sensor 1. In the region 7 in which corrosion thickness of the metal thin film 2 is equal to thickness of the metal thin film 2, therefore, corrosion does not further progress in the thickness direction of the metal thin film 2. When the region 7 is observed through the transparent substrate 3, a color of the region 7 is visually changed from a color of the metal of the metal thin film 2 to a color of a corrosion product of the metal thin film 2 (substance produced through corrosion of the metal thin film 2).

Further, in the region 7' in which the metal thin film is partially corroded in the thickness direction, when the region 7' is observed through the transparent substrate 3, a color of the region 7' is visually changed from the color of the metal of the metal thin film 2. The color is also visually different from the color of the corrosion product of the metal thin film 2.

As described above, in the corrosive environment monitoring method described in the first embodiment, the degree of discoloration of the metal thin film 2 is observed from the two discolored regions (the regions 7 and 7').

Figure 5:
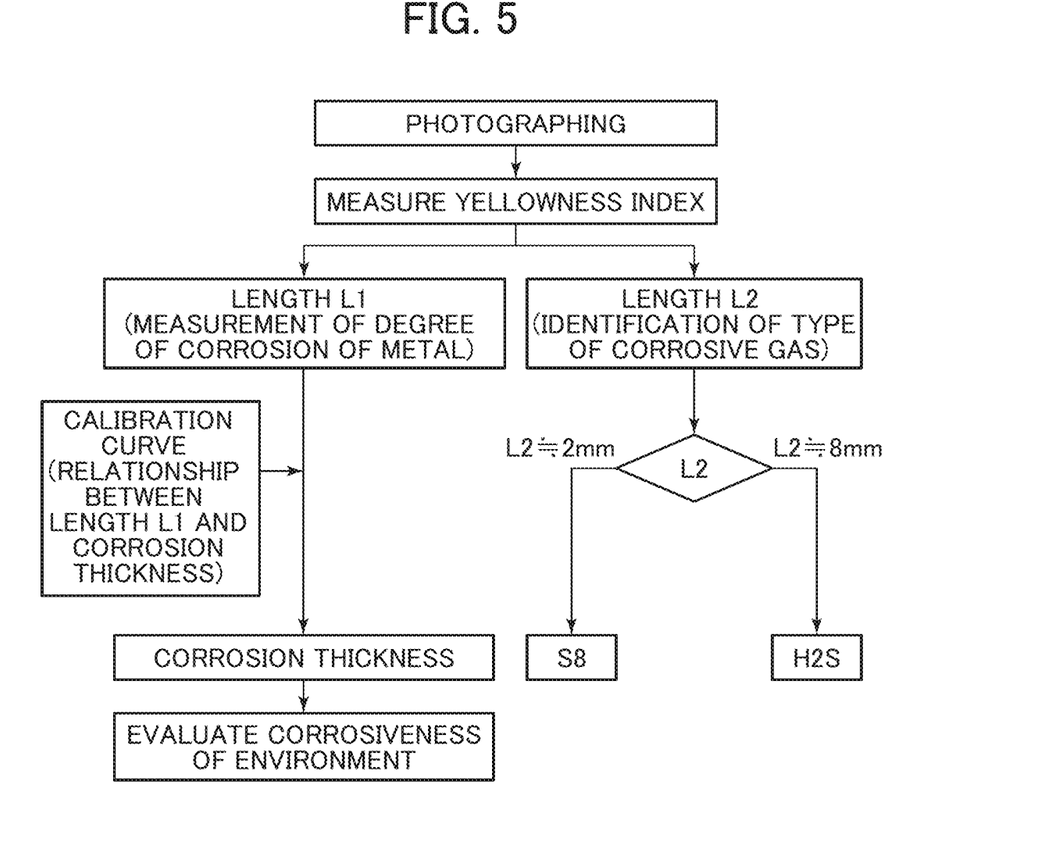
FIG. 5 is a schematic illustration of a corrosive environment monitoring method of the embodiment.

FIG. 5 is a schematic illustration of the corrosive environment monitoring method of the first embodiment. FIG. 5 illustrates a procedure of identifying a type of the corrosive gas and a procedure of measuring the corrosion degree of the metal in the corrosive environment monitoring method.

The photographing unit 11 (see FIG. 1) is used to photograph the corrosion sensor 1 (the degree of discoloration of the metal thin film 2 through the transparent substrate 3).

The image processing unit 12 (see FIG. 1) is used to calculate a yellowness index from the image photographed by the photographing unit 11. A yellowness index profile is then calculated from the opening 5 toward the surface opposed to the opening 5. In a calculation method of the yellowness index, the yellowness index is obtained from a photographed color picture according to JIS K7373 "Determination of yellowness index and change of yellowness index". Specifically, the image photographed by the photographing unit 11 is used to digitize the degree of discoloration of the metal thin film 2. The yellowness index is calculated using the XYZ color system or the $X_{10}Y_{10}Z_{10}$ color system depending on the standard illuminant or the auxiliary illuminant used for the measurement. The same calculating formula as in ASTM 313-00 is used. ASTM 313-05 can also be referenced.

In calculation of the yellowness index, a distance from the opening 5 to the surface opposed to the opening 5 is divided into predetermined intervals (for example, 0.1 mm pitch or 0.2 mm pitch), and a yellowness index is obtained at a position corresponding to each pitch. The yellowness index profile (distribution) corresponds to continuous expression of the yellowness index at each pitch from the opening 5 to the surface opposed to the opening 5.

The calculation unit 13 (see FIG. 1) is used to identify a type of the corrosive gas 6 from the degree of discoloration of the metal thin film 2 digitized by the image processing unit 12 and calculate the degree of corrosion of the metal by the corrosive gas 6.

In identification of the type of the corrosive gas 6, the length L2 is measured from a change point of the yellowness index in the yellowness index profile (an inflexion point in "relationship between a gradient of yellowness index and a distance from the opening 5" as described later). The type of the corrosive gas can be identified from the length L2.

In an environment containing $H_2S$, since the length L2 is nearly equal to 8 mm, if measured L2 is nearly equal to 8 mm, $H_2S$ is identified to exist. In an environment containing $S_8$, since the length L2 is nearly equal to 2 mm, if measured L2 is nearly equal to 2 mm, $S_8$ is identified to exist.

In the first embodiment, the corrosion sensor 1 described in the first embodiment is beforehand exposed to an environment containing $H_2S$ or $S_8$, and the respective lengths L2 are measured for $H_2S$ and $S_8$ each being the corrosive gas 6. As a result, L2 is nearly equal to 8 mm when $H_2S$ is contained, while L2 is nearly equal to 2 mm when $S_8$ is contained. Using such results, for an environment where which corrosive gas 6 is generated is unknown between $H_2S$ and $S_8$, the length L2 is measured after the corrosion sensor 1 described in the first embodiment is installed in the environment, thereby which corrosive gas 6 is generated between $H_2S$ and $S_8$ can be identified.

In other words, even if an environment in which $H_2S$ is generated is difficult to be discriminated from an environment in which $S_8$ is generated, the first embodiment allows such discrimination.

For a type of another corrosive gas 6, the length L2 is beforehand measured, and a result of such measurement is compared with a length L2 measured in actual environment, thereby the type of the corrosive gas 6 can also be identified.

As described above, in the first embodiment, a relationship between the beforehand observed degree of discoloration of the metal thin film 2 (corresponding to length L2) and a type of the corrosive gas 6 is grasped, and the grasped relationship is compared with the actually observed degree of discoloration of the metal thin film 2 (also corresponding to length L2), thereby the type of the corrosive gas 6 can be identified.

The reason for a difference in length L2 of the region 7' of the metal thin film 2 between the $H_2S$ environment and the $S_8$ environment can be explained by a difference in diffusion coefficient between $H_2S$ and $S_8$ each being the corrosive gas 6. Although the $H_2S$ environment and the $S_8$ environment are mentioned herein, another corrosive gas 6 (corrosive gas 6 having a different diffusion coefficient) can also be identified in type by obtaining the length L2 of the region 7' of the metal thin film 2.

With the corrosion degree of the metal, the length L1 is measured from the change point of the yellowness index in the yellowness index profile. The corrosion degree of the metal can be represented in terms of corrosion thickness of a metal plate subjected to exposure. The corrosion thickness of the metal plate is calculated from the length L1 using a calibration curve indicating a relationship between the length L1 and corrosion thickness of the metal plate. The corrosion thickness of the metal plate is used to evaluate corrosiveness of environment. In other words, the length L1 can be used to evaluate the corrosiveness of environment. Ranking is performed according to the corrosion thickness of the metal plate, and corrosiveness of environment is evaluated depending on the ranks.

Another corrosive gas 6 (corrosive gas 6 having a different diffusion coefficient) can also be evaluated in corrosiveness of environment by obtaining the length L1 of the region 7 of the metal thin film 2.

For example, according to the first embodiment, corrosiveness in a relatively clean environment after short exposure for one month can be evaluated according to the ASHRAE guideline, and corrosiveness in a relatively contaminated environment after long exposure for one year can also be evaluated according to ISO 11844-1.

Figure 6:
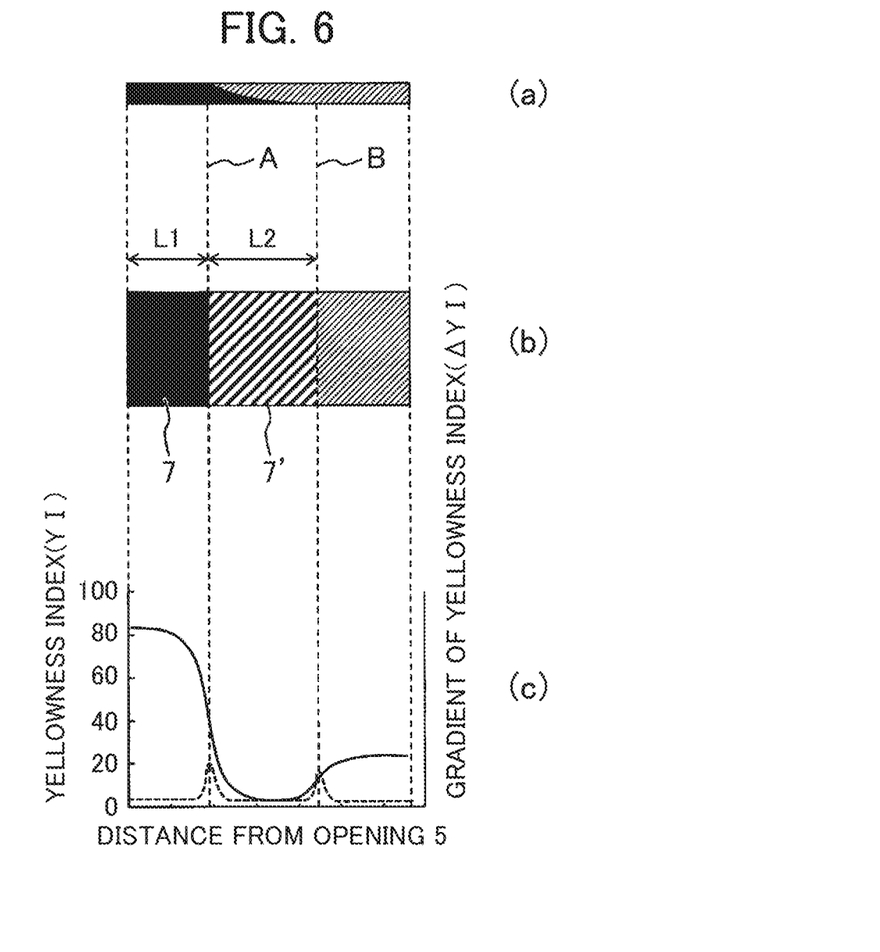
FIG. 6 is a schematic illustration of a state of a metal thin film of the corrosion sensor (film 40 nm or less thick) of the embodiment after exposure.

FIG. 6 is a schematic illustration of a state of the metal thin film of the corrosion sensor (film 40 nm or less thick) of the first embodiment after exposure. In FIG. 6, (a) shows a cross-sectional view of the metal thin film 2 of the corrosion sensor 1 (film 40 nm or less thick) of the first embodiment after exposure, (b) shows a top view of the metal thin film 2 of the corrosion sensor 1 (film 40 nm or less thick) of the first embodiment after exposure, and (c) shows a relationship between a distance from the opening 5 and an yellowness index (solid line) of the metal thin film 2 of the corrosion sensor 1 (film 40 nm or less thick) of the first embodiment after exposure and a relationship between the distance from the opening 5 and a gradient (dotted line) of the yellowness index.

In the first embodiment, the yellowness index profile is created using the yellowness index, and the length L1 of the region 7 of the metal thin film 2 and the length L2 of the region 7' of the metal thin film are measured from the yellowness index profile.

In the corrosion sensor 1 using a metal thin film 2 having a thickness of 40 nm or less, the region 7 of the metal thin film 2 is discolored to yellow, and the region 7' of the metal thin film 2 is discolored to black, and thus a boundary (a spot having a large gradient of the yellowness index) can be determined through evaluation using the yellowness index profile.

Specifically, when the gradient (dotted line) of the yellowness index is calculated from the yellowness index (solid line) in the yellowness index profile, a peak appears in each of the points A and B, and the respective lengths L1 and L2 of the regions 7 and 7' of the metal thin film 2 can be measured from the peaks.

The respective lengths L1 and L2 of the regions 7 and 7' of the metal thin film 2 may be visually measured, if possible. The length L1 and the length L2 are not limitedly measured by the method of using the yellowness index. Another method, e.g., a method focusing on color (method using tint) may be used as long as the respective lengths L1 and L2 of the regions 7 and 7' of the metal thin film 2 can be measured by the method.

As described above, the corrosive environment monitoring method described in the first embodiment identifies a type of the corrosive gas 6 using the length (length L2) of the region (region 7') in which the metal thin film 2 is partially corroded in the thickness direction. In the corrosive environment monitoring method described in the first embodiment, two discolored regions (the regions 7 and 7') are measured from the yellowness index profile.

Figure 7:
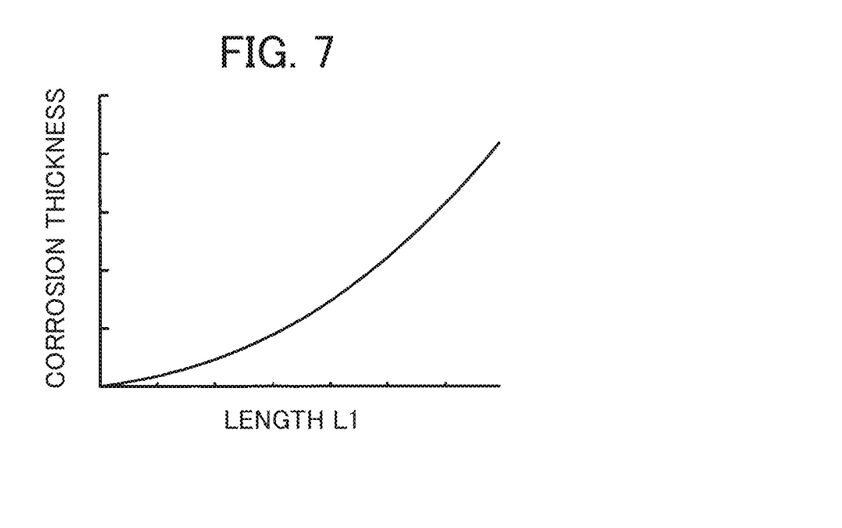
FIG. 7 is a schematic illustration of a relationship between length of a discolored region of a metal thin film of the embodiment and corrosion thickness of a metal plate.

FIG. 7 is a schematic illustration of a relationship between length of the discolored region of the metal thin film of the first embodiment and corrosion thickness of the metal plate. FIG. 7 shows a calibration line indicating a relationship between the length L1 of the region 7 of the metal thin film 2 and corrosion thickness of the metal plate (thickness of the corrosion product of the metal plate).

Such a calibration line can be beforehand created to obtain the corrosion thickness of the metal plate from the measured length L1 of the region 7 of the metal thin film 2.

In other words, the calibration line in the first embodiment indicates the relationship between the length L1 of the region 7 of the metal thin film 2 and corrosion thickness of the metal plate. The thickness of the corrosion product of the metal plate (corrosion thickness of the metal plate) obtained from the calibration line is referred to the ASHRAE guideline or ISO 11844-1 to evaluate corrosiveness of environment.

Figure 8:
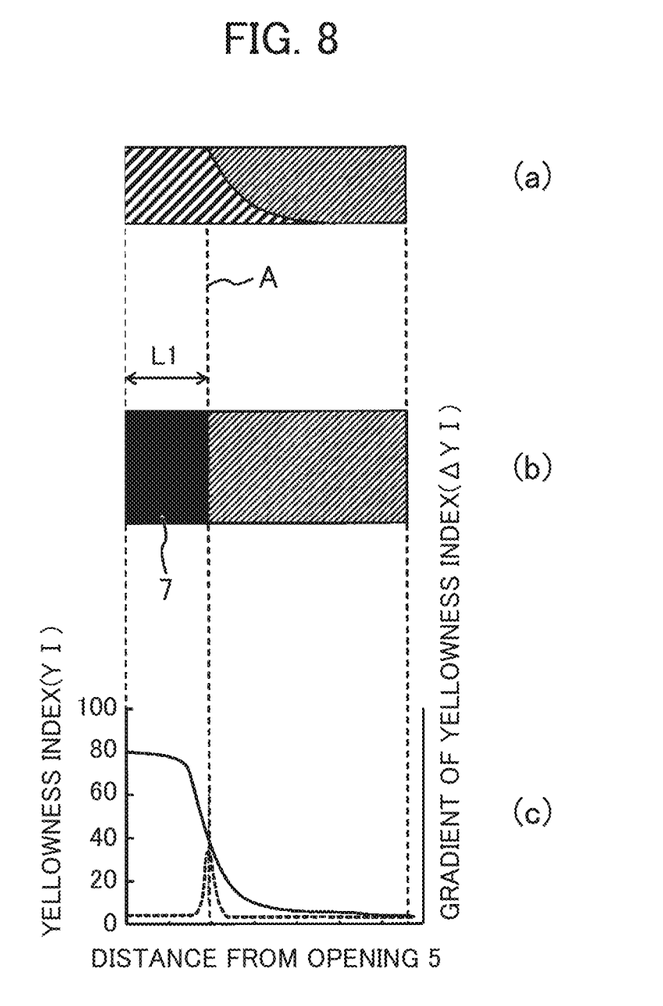
FIG. 8 is a schematic illustration of a state of a metal thin film of a corrosion sensor (film more than 40 nm thick) of a comparative example of the embodiment after exposure.

FIG. 8 is a schematic illustration of a state of a metal thin film of a corrosion sensor (film more than 40 nm thick) of a comparative example of the first embodiment after exposure. In FIG. 8, (a) shows a cross-sectional view of a metal thin film 2 of a corrosion sensor 1 as a target for comparison with the first embodiment after exposure, (b) shows a top view of the metal thin film 2 of the corrosion sensor 1 as the target for comparison with the first embodiment after exposure, and (c) shows a relationship between a distance from the opening 5 and an yellowness index (solid line) of the metal thin film 2 of the corrosion sensor 1 as the target for comparison with the first embodiment after exposure and a relationship between the distance from the opening 5 and a gradient (dotted line) of the yellowness index.

Thus, in the corrosion sensor 1 using the metal thin film 2 having a thickness of more than 40 nm, although the length L1 of the region 7 of the metal thin film 2 can be measured, the length L2 of the region 7' of the metal thin film 2 cannot be measured. This is because since the metal thin film 2 has a large thickness and thus has a high reflectivity, the length L2 of the region 7' of the metal thin film 2 cannot be detected.

The thickness of the metal thin film 2 is therefore preferably 40 nm or less, more preferably 30 nm or less. In the first embodiment, the thickness of the metal thin film 2 is specified to 20 nm. The thickness of the metal thin film 2 is preferably 5 nm or more.

Figure 9:
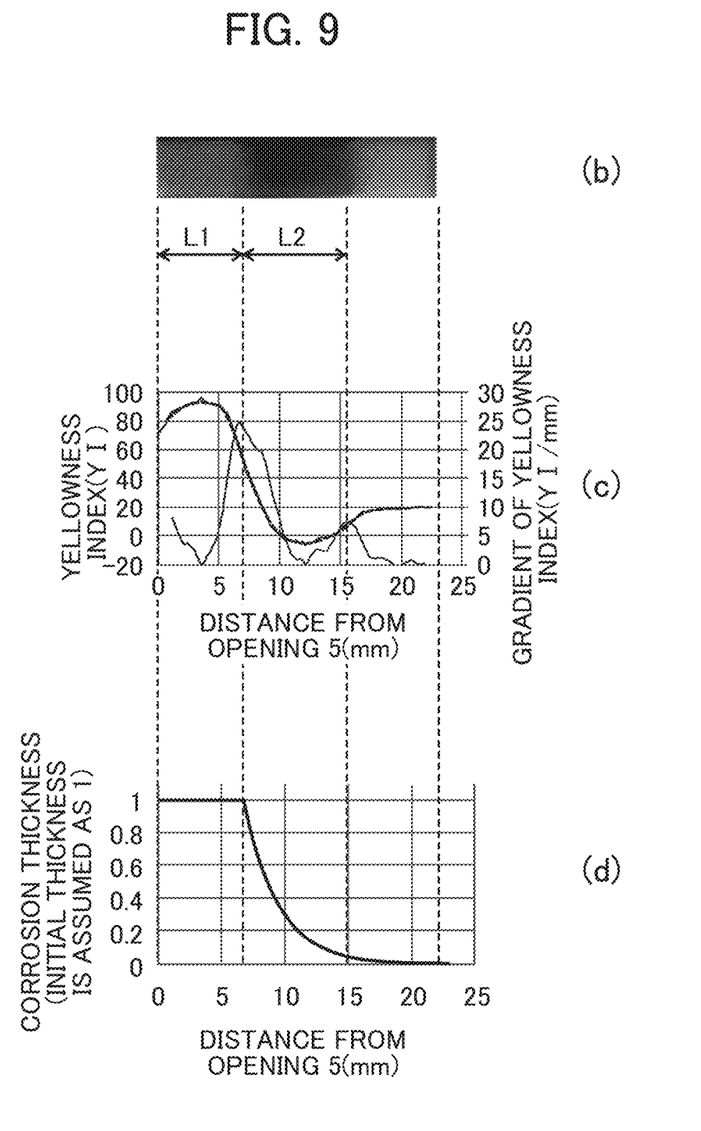
FIG. 9 is a schematic illustration of a state of the metal thin film of the corrosion sensor (film 40 nm or less thick) of the embodiment after exposure in $H_2S$ environment.

FIG. 9 is a schematic illustration of a state of the metal thin film of the corrosion sensor (film 40 nm or less thick) of the first embodiment after exposure in $H_2S$ environment. In FIG. 9, (b) shows a top view (photograph) of the metal thin film 2 of the corrosion sensor 1 (film 40 nm or less thick) of the first embodiment after exposure in $H_2S$ environment, (c) shows a relationship between a distance from the opening 5 and an yellowness index (dotted line) of the metal thin film 2 of the corrosion sensor 1 (film 40 nm or less thick) of the first embodiment after exposure in $H_2S$ environment and a relationship between the distance from the opening 5 and a gradient (thin solid line) of the yellowness index, and (d) shows a relationship between the distance from the opening 5 and corrosion thickness of the metal thin film 2 of the corrosion sensor 1 (film 40 nm or less thick) of the first embodiment after exposure in $H_2S$ environment.

The top view (photograph) (b) of the metal thin film 2 of the corrosion sensor 1 after exposure in $H_2S$ environment is used to obtain a yellowness index profile (c) from the photograph according to the procedure illustrated in FIG. 5. Values of the lengths L1 and L2 obtained from (c) are consistent with analytical results. Specifically, the length L2 as an index to identify a type of the corrosive gas 6 is nearly equal to 8 mm in $H_2S$ environment. However, such a value is given in the case where height of the opening 5 is 1 mm. When height of the opening 5 is 2 mm, the length L2 is approximately 11 mm.

As height of the opening 5 increases, the length L2 increases, and a boundary of each of the regions 7 and 7' of the metal thin film 2 tends to be more unclear. The height of the opening 5 is preferably 2 mm or less.

In addition, (d) shows the relationship between the distance from the opening 5 and corrosion thickness of the metal thin film 2 of the corrosion sensor 1 after exposure in $H_2S$ environment.

Figure 10:
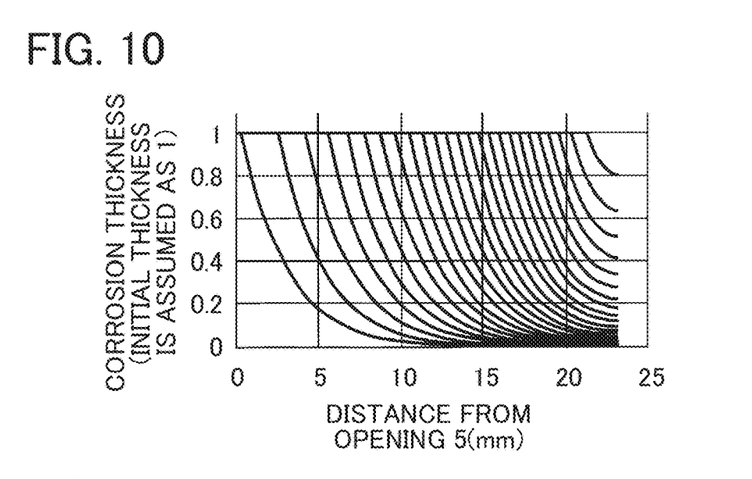
FIG. 10 is a schematic illustration of an analyzed relationship between a distance from an opening and corrosion thickness of a sectional method of a metal thin film of the corrosion sensor (film 40 nm or less thick) of the embodiment after exposure in $H_2S$ environment (every given time interval).

FIG. 10 is a schematic illustration of an analyzed relationship between a distance from the opening and corrosion thickness of a sectional method of the metal thin film of the corrosion sensor (film 40 nm or less thick) of the first embodiment after exposure in $H_2S$ environment (every given time interval).

As illustrated in FIG. 10, although the length L1 elongates over time, the length L2 is constant, i.e., nearly equal to 8 mm. The gradient (gradient while the corrosion thickness decreases from 1 to 0 as away from the opening 5) also does not change.

Figure 11:
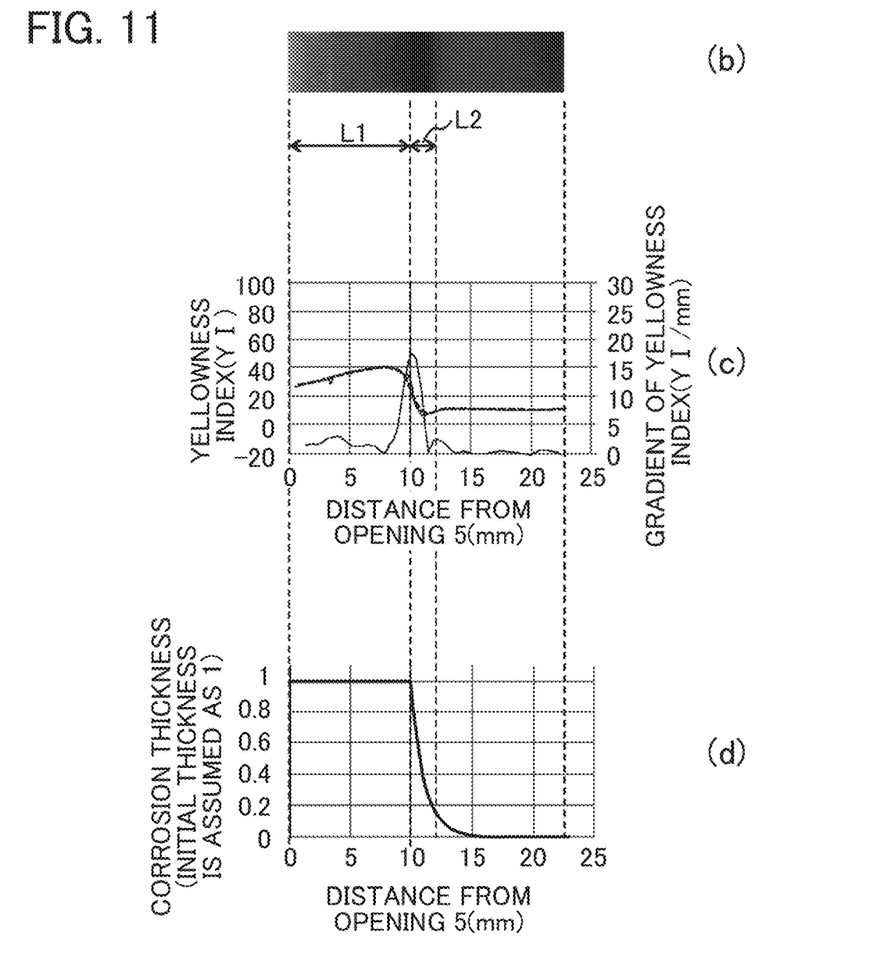
FIG. 11 is a schematic illustration of a state of the metal thin film of the corrosion sensor (film 40 nm or less thick) of the embodiment after exposure in $S_8$ environment.

FIG. 11 is a schematic illustration of a state of the metal thin film of the corrosion sensor (film 40 nm or less thick) of the first embodiment after exposure in $S_8$ environment. In FIG. 11, (b) shows a top view (photograph) of the metal thin film of the corrosion sensor 1 (film 40 nm or less thick) of the first embodiment after exposure in $S_8$ environment, (c) shows a relationship between a distance from the opening 5 and an yellowness index (dotted line) of the metal thin film 2 of the corrosion sensor 1 (film 40 nm or less thick) of the first embodiment after exposure in $S_8$ environment and a relationship between the distance from the opening 5 and a gradient (thin solid line) of the yellowness index, and (d) shows a relationship between the distance from the opening 5 and corrosion thickness of the metal thin film 2 of the corrosion sensor 1 (film 40 nm or less thick) of the first embodiment after exposure in $S_8$ environment.

The top view (photograph) (b) of the metal thin film 2 of the corrosion sensor 1 after exposure in $S_8$ environment is used to obtain a yellowness index profile (c) from the photograph according to the procedure illustrated in FIG. 5. Values of the lengths L1 and L2 obtained from (c) are consistent with analytical results. Specifically, the length L2 as an index to identify a type of the corrosive gas 6 is nearly equal to 2 mm in $S_8$ environment. However, such a value is given in the case where height of the opening 5 is 1 mm. When height of the opening 5 is 2 mm, the length L2 is approximately 4 mm.

As height of the opening 5 increases, the length L2 increases, and a boundary of each of the regions 7 and 7' of the metal thin film 2 tends to be more unclear. The height of the opening 5 is preferably 2 mm or less.

In addition, (d) shows the relationship between the distance from the opening 5 and corrosion thickness of the metal thin film 2 of the corrosion sensor 1 after exposure in $S_8$ environment.

Figure 12:
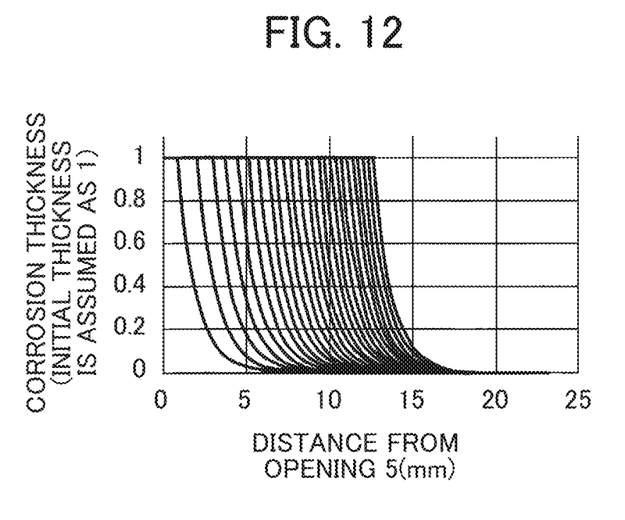
FIG. 12 is a schematic illustration of an analyzed relationship between a distance from an opening and corrosion thickness of a sectional direction of a metal thin film of the corrosion sensor (film 40 nm or less thick) of the embodiment after exposure in $S_8$ environment (every given time interval).

FIG. 12 is a schematic illustration of an analyzed relationship between a distance from the opening and corrosion thickness of a sectional method of the metal thin film of the corrosion sensor (film 40 nm or less thick) of the first embodiment after exposure in $S_8$ environment (every given time interval).

As illustrated in FIG. 12, although the length L1 elongates over time, the length L2 is constant, i.e., nearly equal to 2 mm. The gradient (gradient while the corrosion thickness decreases from 1 to 0 as away from the opening 5) also does not change.

As described above, according to the first embodiment, the degree of discoloration of the metal thin film 2 is observed, and a type of the corrosive gas in an environment, in which an electric or electronic device is installed, can be identified from a relationship between the beforehand observed degree of discoloration of the metal thin film 2 and a type of the corrosive gas 6.

According to the first embodiment, even in an environment in which the electric or electronic device is installed, corrosiveness of environment can be evaluated by observing the corrosion sensor 1, and such a corrosion sensor 1 can be installed in the inside of the housing of the electric or electronic device packaged in high density.

Further, according to the first embodiment, the corrosion sensor 1 can be easily installed in the inside of the housing of the electric or electronic device to evaluate corrosiveness of environment.

According to the first embodiment, an environment in which $H_2S$ is generated can be discriminated from an environment in which $S_8$ is generated, and thus corrosiveness of environment can be accurately evaluated.

According to the first embodiment, a type of corrosive gas 6 can be identified in situ over both short and long periods without need of a power source such as a commercial power source and a storage battery even in a narrow space inside a housing of an electric or electronic device to be evaluated without need of any special analytical equipment. In addition, the corrosion degree of metal can be measured.

Specifically, the first embodiment can address sulfidation corrosion trouble frequently reported in recent years to identify a type of the corrosive gas 6 as reducing sulfur and discriminate between the corrosive gases of $H_2S$ and $S_8$.

Typically, for example, when silver is exposed in an environment containing reducing sulfur, corrosiveness of environment is evaluated from silver sulfide ($Ag_2S$) as a corrosion product of silver. However, silver sulfide ($Ag_2S$) is generated in both the environment in which $H_2S$ is generated and the environment in which $S_8$ is generated, and thus which is generated between $H_2S$ and $S_8$ is difficult to be determined. Which is generated between $H_2S$ and $S_8$ is therefore unknown, and thus it is difficult to specify a source of the corrosive gas 6 on-site, and consequently corrosiveness of environment has not been accurately evaluated. The first embodiment successfully solves such a problem.

The invention should not be limited to the above-described embodiment, and includes various modifications and alterations. For example, the above-described embodiment has been described in detail to clearly explain the invention, and the invention is not necessarily limited to the embodiment having all the described configurations.

LIST OF REFERENCE SIGNS

1 Corrosion sensor
2 Metal thin film
3 Transparent substrate
4 Passage structure
5 Opening
6, 6' Corrosive gas
7 Region in which metal thin film 2 is entirely corroded in thickness direction
7' Region in which metal thin film 2 is partially corroded in thickness direction
10 Determination system
11 Photographing unit
12 Image processing unit
13 Calculation unit
14 Output unit

The invention claimed is:

1. A corrosive environment monitoring method, the method using a corrosion sensor including a passage structure having a first end being closed and a second end as an opening, one of the upper and lower surfaces or left and right surfaces with respect to the opening being formed of a transparent substrate, the corrosion sensor further including a metal thin film having a first surface formed on a surface of the transparent substrate, a second surface of the metal thin film opposite to the first surface being in contact with corrosive gas flowing in from the opening, wherein the degree of discoloration of the metal thin film is observed through the transparent substrate, and a type of the corrosive gas is identified from a relationship between a beforehand observed degree of discoloration of the metal thin film and a type of the corrosive gas, wherein the metal thin film has a thickness of 5 to 40 nm.

2. The corrosive environment monitoring method according to claim 1, wherein the degree of discoloration of the metal thin film is observed from two discolored regions.

3. The corrosive environment monitoring method according to claim 2, wherein the two discolored regions are measured from a yellowness index profile.

4. The corrosive environment monitoring method according to claim 1, wherein the type of the corrosive gas is identified using length of a region in which the metal thin film is partially corroded in a thickness direction.

5. The corrosive environment monitoring method according to claim 1, wherein the opening has a height of 0.5 to 2.0 mm.

6. The corrosive environment monitoring method according to claim 1, wherein the metal thin film is a silver film, and types of two corrosive gases of $H_2S$ and $S_8$ are identified.

7. A corrosive environment monitoring system, comprising:
a photographing sensor configured to take a photograph of a discoloration degree of a metal thin film of a corrosion sensor including a passage structure having a first end being closed and a second end as an opening, one of the upper and lower surfaces or left and right surfaces with respect to the opening being formed of a transparent substrate, the metal thin film having a first surface being formed on a surface of the transparent substrate, a second surface of the metal thin film opposite to the first surface being in contact with corrosive gas flowing in from the opening;
an image processor configured to use an image photographed by the photographing sensor to digitize the discoloration degree of the metal thin film;
a calculation processor configured to identify a type of the corrosive gas from the discoloration degree of the metal thin film digitized by the image processor and a relationship between a beforehand observed degree of discoloration of the metal thin film and a type of the corrosive gas; and
an output configured to output a result of calculation by the calculation processor,
wherein the metal thin film has a thickness of 5 to 40 nm.

* * * * *